US012642783B2

(12) United States Patent
Duquesroix-Chakroun et al.

(10) Patent No.: US 12,642,783 B2
(45) **Date of Patent: *Jun. 2, 2026**

(54) METHOD FOR TREATING VASO OCCLUSIVE CRISES ASSOCIATED WITH SICKLE CELL DISEASE

(71) Applicants: Nicox SA, Sophia Antipolis (FR); Fera Pharmaceuticals, LLC., Locust Valley, NY (US)

(72) Inventors: Brigitte Duquesroix-Chakroun, Cagnes sur Mer (FR); Frank J. Dellafera, Locust Valley, NY (US); Scott Florentino, Locust Valley, NY (US)

(73) Assignees: NICOX SA, Sophia Antipolis (FR); FERA PHARMACEUTICALS, LLC., Locust Valley, NY (US)

( * ) Notice: Subject to any disclaimer, the term of this patent is extended or adjusted under 35 U.S.C. 154(b) by 378 days.

This patent is subject to a terminal disclaimer.

(21) Appl. No.: 18/304,153

(22) Filed: Apr. 20, 2023

(65) Prior Publication Data

US 2023/0255918 A1 Aug. 17, 2023

Related U.S. Application Data

(62) Division of application No. 17/170,319, filed on Feb. 8, 2021, now Pat. No. 11,660,282.

(60) Provisional application No. 62/972,508, filed on Feb. 10, 2020.

(51) Int. Cl.

*A61K 31/222* (2006.01)
*A61P 9/10* (2006.01)

(52) U.S. Cl.

CPC .............. *A61K 31/222* (2013.01); *A61P 9/10* (2018.01)

(58) Field of Classification Search

CPC .................................................... A61K 31/222

See application file for complete search history.

(56) References Cited

U.S. PATENT DOCUMENTS

| | | | |
|---|---|---|---|
| 11,660,282 B2 * | 5/2023 | Duquesroix-Chakroun ................ A61K 31/222 514/534 | |
| 2008/0269323 A1 | 10/2008 | Prasad et al. | |
| 2016/0113936 A1 | 4/2016 | Brittain et al. | |

OTHER PUBLICATIONS

Schnitzer T.J. et al, Osteoarthritis and Cartilage 18 (2010) 629-639.
White W. B. et al., (Am J Cardiol 2011; 107:1338-1345).
(Belanger AM, Keggi C, Kanias T, et al. Effects of nitric oxide and its congeners on sickle red blood cell deformability. Transfusion, 2015 (55) 2464-2472).
(Helms CC, Marvel M, Zhao W, Stahle M, Vest R, Kato GJ, et al. Mechanisms of hemolysis-associated platelet activation. Journal of Thrombosis and Haemostasis. 2013; 11(12): 2148-2154.
Villagra J, Shiva S, Hunter LA, Machado RF, Gladwin MI, Kato GJ. Platelet activation in patients with sickle disease, hemolysis-associated pulmonary hypertension, and nitric oxide scavenging by cell-free hemoglobin. Blood 2007; 110 (6): 2166-2172).
(Parise LV, Telen MJ. Erythrocyte adhesion in sickle cell disease. Current Hematology Reports. 2003; 2(2): 102-108., 2003.
Hoppe CC. Inflammatory mediators of endothelial injury in Sickle Cell Disease. Hematol Oncol Clin. North Am. 2014; 28(2): 265-.
Kutlar A, Embury SH. Cellular adhesion and the endothelium: P-Selectin. Hematol Oncol Clin. North Am. 2014; 28(2): 323-339.
Zhang DC, Xu CL, Manwani D, Frenette PS. Neutrophils, platelets, and inflammatory pathways at the nexus of sickle cell disease pathophysiology. Blood. 2016; 127(7): 801-839.
Kim-Shapiro DB, Gladwin MT. Nitric oxide pathology and therapeutics in sickle cell disease. Clinical Hemorheology and Microcirculation, 2018; 68: 223-237).
(Ballas SK, Gupta K, Adams-Graves P. Sickle cell pain: a critical reappraisal Blood, 2012; 120(18): 3647-3656).
Ballas SK. Pain management of sickle cell disease. Hematol Oncol Clin North Am. 2005;19(5): 785-802.
Ballas SK. Current issues in sickle cell pain and its management. Hematology Am Soc Hematol Educ Program. 2007; 97-105).
(Goncalves R. P., Rev Bras Hematol Hemoter 2012;34(4):254-64).

* cited by examiner

*Primary Examiner* — John S Kenyon
(74) *Attorney, Agent, or Firm* — ArentFox Schiff LLP

(57) ABSTRACT

The present invention relates to a treatment of vaso-occlusive crisis (VOC) associated with Sickle cell disease by administering a therapeutically effective amount of 4-(nitrooxy)butyl-(2S)-2-(6-methoxy-2-naphthyl) propanoate.

8 Claims, 1 Drawing Sheet

Naproxcinod increases nitrite concentrations in the plasma. N=4-7; *p<0.01

Naproxcinod increases platelet cGMP production. N=4-7; *p<0.01

METHOD FOR TREATING VASO OCCLUSIVE CRISES ASSOCIATED WITH SICKLE CELL DISEASE

CROSS REFERENCE TO RELATED APPLICATIONS

This application is a Divisional of U.S. patent application Ser. No. 17/170,319, filed Feb. 8, 2021, which claims the benefit of U.S. Provisional Application No. 62/972,508, filed Feb. 10, 2020, the contents of all of the above applications are incorporated herein by reference in their entireties.

FIELD OF THE INVENTION

The present invention relates to a treatment of Sickle cell disease vaso-occlusive crisis (VOC) by administering a therapeutically effective amount of 4-(nitrooxy)butyl-(2S)-2-(6-methoxy-2-naphthyl) propanoate.

BACKGROUND OF THE INVENTION 4-(nitrooxy)butyl-(2S)-2-(6-methoxy-2-naphthyl) propanoate is a Nitric Oxide (NO) releasing derivative of naproxen and it is also known as Naproxcinod.

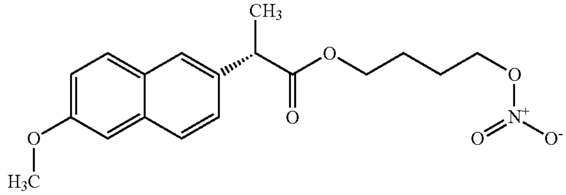

4-(nitrooxy)butyl-(2S)-2-(6-methoxy-2-naphthyl) propanoate

WO 98/09831 and U.S. Pat. No. 6,700,011 disclose the synthesis of 4-(nitrooxy)butyl-(2S)-2-(6-methoxy-2-naphthyl) propanoate.

Schnitzer T. J. et al, Osteoarthritis and Cartilage 18 (2010) 629-639 discloses that naproxinod is a NO releasing derivative of naproxen that combines analgesic and anti-inflammatory effects with blood pressure effects similar to placebo and different from naproxen. In human studies in osteoarthritis (OA) of the knee patients, naproxcinod showed clinical efficacy and safety in the management of the signs and symptoms of OA.

White W. B. et al, (Am J Cardiol 2011; 107:1338-1345) discloses a large-scale analysis of the effects of naproxcinod on blood pressure in 3 pivotal trials involving 2,734 patients with osteoarthritis of the hip or knee. The results of the analysis demonstrated that naproxcinod can reduce some of the hypertensive burden induced by most NSAIDs.

Sickle cell disease (SCD), is a group of hemoglobinopathies caused by mutations in the sixth amino acid of the β-globin subunit of hemoglobin. The most common mutation, βS-globin, results in the replacement of the hydrophilic glutamic acid residue by the hydrophobic valine leading to the production of hemoglobin S with the propensity to undergo polymerization upon de-oxygenation (Belanger A M, Keggi C, Kanias T, et al. Effects of nitric oxide and its congeners on sickle red blood cell deformability. *Transfusion,* 2015 (55) 2464-2472).

The polymerization of HbS under hypoxic conditions distorts red blood cells into the characteristic sickle shape, and increases rigidity and fragility resulting in hemolysis. Hemolysis in turn contributes to oxidative stress and platelet activation (Helms C C, Marvel M, Zhao W, Stahle M, Vest R, Kato G J, et al. Mechanisms of hemolysis-associated platelet activation. *Journal of Thrombosis and Haemostasis.* 2013; 11(12): 2148-2154; Villagra J, Shiva S, Hunter L A, Machado R F, Gladwin M I, Kato G J. Platelet activation in patients with sickle disease, hemolysis-associated pulmonary hypertension, and nitric oxide scavenging by cell-free hemoglobin. *Blood* 2007; 110(6): 2166-2172). The oxidative stress, physical interactions of sickled cells with the endothelium and other factors result in an inflammatory state where endothelial cells and leukocytes are activated resulting in leucocyte and multi-cellular adhesion to the endothelium leading to VOC. Ischemia, organ damage, pain and potentially death are all secondary to VOC (Parise L V, Telen M J. Erythrocyte adhesion in sickle cell disease. Current Hematology Reports. 2003; 2(2): 102-108., 2003; Hoppe C C. Inflammatory mediators of endothelial injury in Sickle Cell Disease. *Hematol Oncol Clin. North Am.* 2014; 28(2): 265-86; Kutlar A, Embury S H. Cellular adhesion and the endothelium: P-Selectin. *Hematol Oncol Clin. North Am.* 2014; 28(2): 323-339; Zhang D C, Xu C L, Manwani D, Frenette P S. Neutrophils, platelets, and inflammatory pathways at the *nexus* of sickle cell disease pathophysiology. *Blood.* 2016; 127(7): 801-839; Kim-Shapiro D B, Gladwin M T. Nitric oxide pathology and therapeutics in sickle cell disease. *Clinical Hemorheology and Microcirculation,* 2018; 68: 223-237).

The vaso-occlusive crises and their accompanying pain are common reasons for emergency department visits and hospitalizations in patients with sickle cell disease. Vaso-occlusive crises and their accompanying pain most commonly occur in the extremities, chest, and back and is considered nociceptive, secondary to tissue damage. Clinical features of a typical painful crisis have been described as having a sudden onset of pain in the low back or in one or more joints or one of the extremities. The pain may be localized or migratory and is continuous and throbbing. The severe pain causes patients to grunt, groan, cry, twist and turn and to assume abnormal postures in the unsuccessful attempt to obtain relief. Severe episodes require treatment at a medical center with parenteral opioids after failed attempts to control the pain with oral narcotic and/or the off-label use of over the counter NSAID medications. (Ballas S K, Gupta K, Adams-Graves P. Sickle cell pain: a critical reappraisal *Blood,* 2012; 120(18): 3647-3656).

Vaso-occlusive painful crisis evolves through four phases: prodromal, initial, established and resolving. Each acute painful episode is associated with inflammation that worsens with recurrent episodes, often culminating in serious complications and organ damage such as acute chest syndrome, multi-organ failure. Prodromal phase is a period before the onset of severe pain and lasts 1-2 days, it is followed by a gradual or sudden increase in pain (initial phase) with a pain peaking after 3 days, which leads to entry into the established phase that lasts up to day 6 or day 7 after that pain starts decreasing (resolving phase). The prodromal phase of the crisis is characterized by three main pathophysiologic events: vaso-occlusion, inflammation and nociception. Therefore, managing the vaso-occlusive crisis at the prodromal phase, where tissue ischemia and inflammation are in the early stage, could potentially prevent or minimize pain and tissue damages. (Ballas S K, Gupta K, Adams-Graves P. Sickle cell pain: a critical reappraisal Blood, 2012; 120(18): 3647-3656).

Currently, the main therapies to manage vaso-occlusive crises include treatment of acute painful episode and reducing the occurrence of vaso-occlusive crises.

Three drugs have been approved by the FDA for the treatment of vaso-occlusive crises complication in sickle cell disease, Droxia® (hydroxyurea), Endari® (L-glutamine) and Adakveo® (crizanlizumab-tmca). All products have been shown to reduce the frequency of vaso-occlusive crises but these drugs have not been shown to reduce the pain associated with VOC.

Recently approved Adakveo lists in its approved package insert incidence rates of 18% for arthralgia and 15% for back pain associated with its product, indicating a continued need for pain relief. (Novartis, 2019)

Unfortunately, while hydroxyurea (Droxia) reduces the incidence of VOC, it does not eliminate VOC, leaving patients in need of pain reduction when painful vaso-occlusive crises do occur. Moreover, Droxia package insert contains a Black Box Warning for myelosuppression and malignancies.

No product is currently approved by FDA for the treatment of pain secondary to vaso-occlusive crisis for patients with sickle cell disease, but various analgesics are commonly used off label. Guidelines recommend the use of NSAIDs for mild to moderate pain, however no NSAID has shown in well controlled clinical trials to have an effect on the pain secondary to VOC.

As the VOC progresses, over 90% of the adult patients will require hospitalization and require treatments for pain including parenteral opioid treatment consisting of meperidine, morphine or hydromorphone. (Ballas S K. Pain management of sickle cell disease. *Hematol Oncol Clin North Am.* 2005; 19(5): 785-802).

Despite opioid treatment is the mainstay of pain therapy, opioid therapy remains a suboptimal approach due to side effects such as sedation, dizziness, nausea, vomiting, constipation, physical dependence, tolerance, and respiratory depression, but also serious adverse effects that occur after high doses or long-term use including opioid tolerance (which leads to increasing doses of opioids), immune suppression, hormonal changes hyperalgesia and an increased risk of acute chest syndrome and altered clearance of opioids in sickle cell patients. (Ballas S K. Current issues in sickle cell pain and its management. *Hematology Am Soc Hematol Educ Program.* 2007; 97-105).

It is well known that Nitric Oxide (NO) a free radical signaling molecule plays a role in a wide range of biologic functions including relaxing blood vessels, increasing blood flow, reducing platelet activation, reducing circulating blood cell adhesion to endothelia and reducing thrombosis. In response to many different stimuli vascular endothelial cells produce Nitric Oxide that activates guanylate cyclase, leading to increased intracellular levels of cyclic GMP (cGMP). Extensive studies have shown that Nitric oxide levels are depleted in Sickle cell disease and are further depleted during VOC (Goncalves R. P., Rev *Bras Hematol Hemoter* 2012; 34(4):254-64).

Therapeutic strategies to supplement or modulate Nitric Oxide (NO) were disclosed as potential treatments of sickle cell disease and/or symptoms.

For example, initial trials showed some positive effects of inhaled NO on acute VOCs. However, the currently available results do not provide sufficient evidence to determine the effects of using inhaled nitric oxide to treat painful (vaso-occlusive) crises in people with sickle cell disease. Moreover, inhaled NO requires specialized handling and administration.

Another disclosed strategy to increase NO production in sickle cell patients is the supplementation of nitric oxide precursors. Summar M. L. et al. (US 2018/0289647) discloses a method for treating sickle cell disease and its complications including vaso-occlusive crises comprising administering citrulline that is a precursor of the endogenous production of arginine and nitric oxide (NO). US 2018/0289647 reports a study that demonstrates the safety and pharmacokinetic profile of intravenous administered citrulline in patients with sickle cell disease. However, the clinical efficacy of citrulline needs to be further evaluated in clinical studies.

Therefore, an effective and safe therapy for treating vaso-occlusive crisis in patients who suffer from sickle cell disease is a critically unmet need.

Applicant has recently conducted pre-clinical studies and found that 4-(nitrooxy)butyl-(2S)-2-(6-methoxy-2-naphthyl)propanoate was able to increase cyclic guanosine monophosphate level (cGMP level) in a Sickle cell animal model, therefore 4-(nitrooxy)butyl-(2S)-2-(6-methoxy-2-naphthyl)propanoate may play a role in mitigating the nitric oxide depletion in Sickle cell patients and in turn improving vascular homeostasis. In addition the anti-inflammatory and analgesic activities of 4-(nitrooxy)butyl-(2S)-2-(6-methoxy-2-naphthyl)propanoate may reduce the inflammatory cascade and pain associated with the vaso-occlusive crisis.

SUMMARY OF THE INVENTION

It has been found that 4-(nitrooxy)butyl-(2S)-2-(6-methoxy-2-naphthyl) propanoate can beneficially interfere with the pathogenesis and relief of painful symptoms and complications associated with sickle cell anemia vaso-occlusive crisis (VOC).

An embodiment of the invention relates to a method of treating vaso-occlusive crisis in a Sickle cell disease patient comprising administering a therapeutically effective amount of a 4-(nitrooxy)butyl-(2S)-2-(6-methoxy-2-naphthyl) propanoate to the patient in need thereof.

Another embodiment of the invention relates to a method of treating vaso-occlusive crisis in a Sickle cell disease patient comprising administering a therapeutically effective amount of a 4-(nitrooxy)butyl-(2S)-2-(6-methoxy-2-naphthyl) propanoate to the patient in need thereof, wherein 4-(nitrooxy)butyl-(2S)-2-(6-methoxy-2-naphthyl) propanoate is administered as soon as the patient feels an impending crisis, preferably at the onset of the early prodromal signs and symptoms of the vaso-occlusive crisis; the administration of 4-(nitrooxy)butyl-(2S)-2-(6-methoxy-2-naphthyl) propanoate starts at the onset of the early prodromal signs and symptoms of the vaso-occlusive crisis and lasts at least until the crisis is managed.

The method of the invention have some advantages: 4-(nitrooxy)butyl-(2S)-2-(6-methoxy-2-naphthyl) propanoate may be administered to the patient at home (self-administration) as soon as the patient feels an impending crisis (prodromal phase); the administration of 4-(nitrooxy)butyl-(2S)-2-(6-methoxy-2-naphthyl) propanoate at an early stage of the vaso-occlusive crisis may help to facilitate and speed up the resolution of the crisis because reduces the cascade of events such as vaso-occlusion, inflammation and pain, that is associated with the vaso-occlusive crisis.

Minimize the vaso-occlusion and inflammation may reduce the organs and tissues damages in sickle cell patients, by reducing (1) the amount of damage that organs and tissues suffer due to ischemia caused by blockage of blood flow through capillaries, (2) the amount of damage caused by oxidative free radicals, in organs and tissues where blood flow has been restored after a period of ischemia (3) inflammatory mediators released from injured cells.

The reduction of the intensity of the pain associated with the vaso-occlusive crisis may reduce or avoid the need of using opioids to cope with acute painful crisis associated with ischemic crises in sickle cell patients and therefore may reduce hospitalization of the patients.

Since 4-(nitrooxy)butyl-(2S)-2-(6-methoxy-2-naphthyl) propanoate is well tolerated, the compound may be administered in conjunction with other medical treatments that are conventionally used to treat SCD, in a manner which does not interfere with such other treatments.

Another embodiment of the invention relates to a method for reducing the severity or duration of the vaso-occlusive events in a subject suffering from sickle cell disease comprising administering a therapeutically effective amount of a 4-(nitrooxy)butyl-(2S)-2-(6-methoxy-2-naphthyl) propanoate.

Another embodiment of this invention is a method of reducing the organs and tissues damages caused by vaso-occlusive events comprising administering to a subject having Sickle cell disease an effective amount of a 4-(nitrooxy)butyl-(2S)-2-(6-methoxy-2-naphthyl) propanoate.

An embodiment of the invention provides a method for treating pain in patients who suffer from Sickle cell anemia, during the recurrent ischemic crises by administering a therapeutically effective amount of 4-(nitrooxy)butyl-(2S)-2-(6-methoxy-2-naphthyl) propanoate.

Another embodiment of the invention is a method for the treatment of pain secondary to Sickle cell disease vaso-occlusive crisis (VOC) in Sickle cell anemia patients by administering an effective amount 4-(nitrooxy)butyl-(2S)-2-(6-methoxy-2-naphthyl) propanoate in conjunction with the opioids therapy used during such painful crises.

In an embodiment, the present invention includes a method of the present invention wherein a therapeutically effective amount of 4-(nitrooxy)butyl-(2S)-2-(6-methoxy-2-naphthyl) propanoate is present in a pharmaceutical composition which further includes one or more pharmaceutically acceptable carriers. In an embodiment the pharmaceutical composition is suitable for oral, nasal, topical, buccal, sublingual, rectal, vaginal or parenteral administration.

DETAILED DESCRIPTION OF THE INVENTION

Figure 1:
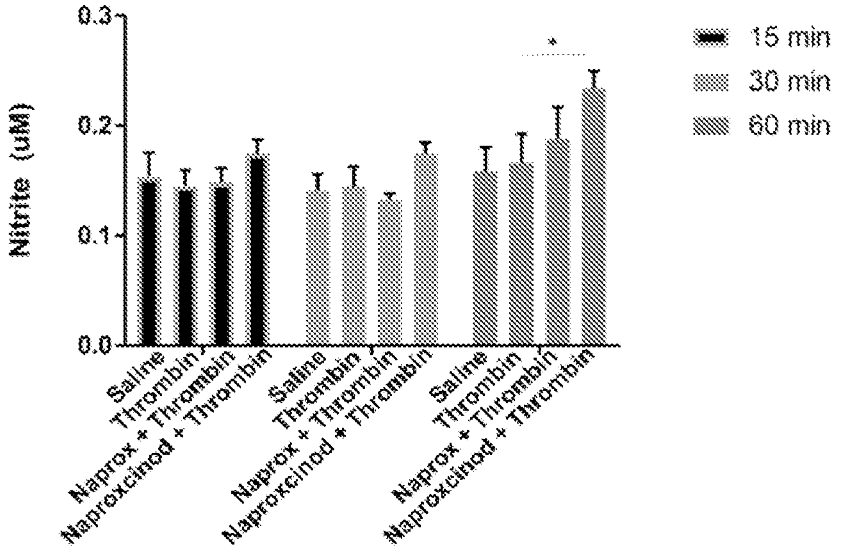
FIG. 1: is a graph showing Nitrite blood concentrations (concentration-time) after intravenous administration of 4-(nitrooxy)butyl-(2S)-2-(6-methoxy-2-naphthyl) propanoate (naproxcinod) or naproxen in homozygous Sickle Cell transgenic mice.

A method is provided for the treatment of the acute pain crisis in a Sickle cell anemia patient. The method includes administering a therapeutically effective amount of 4-(nitrooxy)butyl-(2S)-2-(6-methoxy-2-naphthyl) propanoate (naproxcinod).

The following description provides specific details in order to provide a thorough understanding of the invention. The skilled artisan, however, would understand that the invention can be practiced without employing these specific details. For purposes of interpreting this specification, the following definitions will apply and whenever appropriate, terms used in the singular will also include the plural and vice versa.

"Treatment" as defined herein means any reduction of the severity or duration of the vaso-occlusive events, to abort a crisis, or any reduction of the pain associated with Sickle cell anemia. The reduction in pain can include the reduction in frequency, duration or intensity of the pain. The intensity of the pain can be measured by standard means, for example, a dolorimeter, a palpometer, 10 points pain scale, etc.

"Prodromal signs and symptoms of the vaso-occlusive crisis" as defined herein includes: tiredness, dizziness, weakness, yellowing of the eyes, pallor, gastrointestinal symptoms such as nausea, vomiting, and change in appetite, musculoskeletal symptoms such as swelling of hands/feet, tenderness, or stiffness in joints as well as respiratory such as sniffling, coughing, and changes in breathing.

As used herein, the term "therapeutically effective amount" of the compound is that amount necessary or sufficient to treat or prevent a disease, disorder, and/or a condition as described herein. The effective amount can vary depending on such factors as the size and weight of the subject, the type of illness, or the particular compound of the invention. One of ordinary skill in the art would be able to study the factors contained herein and make the determination regarding the effective amount of the compound of the invention without undue experimentation.

Actual dosage levels of the active ingredients in the pharmaceutical compositions of this invention may be varied so as to obtain an amount of the active ingredient which is effective to achieve the desired therapeutic response for a particular patient, composition, and mode of administration, without being toxic to the patient.

The selected dosage level will depend upon a variety of factors including the activity of the particular compound of the present invention employed the route of administration, the time of administration, the rate of excretion of the particular compound being employed, the duration of the treatment, other drugs, compounds and/or materials used in combination with the particular compound employed, the age, sex, weight, condition, general health and prior medical history of the patient being treated, and like factors well known in the medical arts.

A physician having ordinary skill in the art can readily determine and prescribe the effective amount of the pharmaceutical composition required. For example, the physician could start doses of the compounds of the invention employed in the pharmaceutical composition at levels lower than that required in order to achieve the desired therapeutic effect and gradually increase the dosage until the desired effect is achieved.

In general, a suitable daily dose of a compound of the invention will be that amount of the compound that is the lowest dose effective to produce a therapeutic effect. Such an effective dose will generally depend upon the factors described above.

If desired, the effective daily dose of the active compound may be administered as two, three, four, five, six or more sub-doses administered separately at appropriate intervals throughout the day, optionally, in unit dosage forms.

While it is possible for a compound of the present invention to be administered alone, it is preferable to administer the compound as a pharmaceutical composition.

For use in the present treatment 4-(nitrooxy)butyl-(2S)-2-(6-methoxy-2-naphthyl) propanoate is administered orally; the dosage for adults ranges from 100 mg/day to 3000 mg/day or from 100 mg/day to 2000 mg/day, preferably from 375 mg/day to 1500 mg/day, most preferably from 750 mg/day to 1500 mg/day; the dosage for children (over 2 years old and under 16 years old) ranges from 15 to 22.5 mg per Kg per day.

The exact dosage and schedule of administration will vary depending on the amount needed to provide relief in each particular instance.

For use in the present treatment, 4-(nitrooxy)butyl-(2S)-2-(6-methoxy-2-naphthyl) propanoate is preferably administered to a patient from the onset of the early prodromal signs and symptoms of the vaso-occlusive crisis until the crisis is managed. The treatment can be also used for maintenance therapy after management of the vaso-occlusive crisis.

The regimen of administration can affect what constitutes an effective amount. Several divided dosages, as well as staggered dosages, can be administered daily or sequentially, or the dose can be continuously infused, or can be a bolus injection. Further, the dosages of the compound of the invention can be proportionally increased or decreased as indicated by the exigencies of the therapeutic or prophylactic situation.

The term "pharmaceutical composition" as used herein includes preparations suitable for administration to mammals, e.g., humans. When the compounds of the present invention are administered as pharmaceuticals to mammals, e.g., humans, they can be given per se or as a pharmaceutical composition containing, for example, 0.1 to 99.5% (more preferably, 0.5 to 90%) of active ingredient in combination with a pharmaceutically acceptable carrier.

The term "pharmaceutically acceptable carrier" as used herein is recognized in the art and includes a pharmaceutically acceptable material, composition or vehicle, suitable for administering compound of the present invention to mammals. The carriers include liquid or solid filler, diluent, excipient, solvent or encapsulating material, involved in carrying or transporting the subject agent from one organ, or portion of the body, to another organ, or portion of the body. Each carrier must be "acceptable" in the sense of being compatible with the other ingredients of the formulation and not injurious to the patient. Some examples of materials which can serve as pharmaceutically acceptable carriers include: sugars, such as lactose, glucose and sucrose; starches, such as corn starch and potato starch; cellulose, and its derivatives, such as sodium carboxymethyl cellulose, ethyl cellulose and cellulose acetate; powdered tragacanth; malt; gelatin; talc; excipients, such as cocoa butter and suppository waxes; oils, such as peanut oil, cottonseed oil, safflower oil, sesame oil, olive oil, corn oil and soybean oil; glycols, such as propylene glycol; polyols, such as glycerin, sorbitol, mannitol and polyethylene glycol; esters, such as ethyl oleate and ethyl laurate; agar; buffering agents, such as magnesium hydroxide and aluminum hydroxide; alginic acid; pyrogen-free water; isotonic saline; Ringer's solution; ethyl alcohol; phosphate buffer solutions; and other non-toxic compatible substances employed in pharmaceutical formulations.

Wetting agents, emulsifiers and lubricants, such as sodium lauryl sulfate and magnesium stearate, as well as coloring agents, release agents, coating agents, sweetening, flavoring and perfuming agents, preservatives and antioxidants can also be present in the compositions.

Examples of pharmaceutically acceptable antioxidants include: water soluble antioxidants, such as ascorbic acid, cysteine hydrochloride, sodium bisulfate, sodium metabisulfite, sodium sulfite and the like; oil-soluble antioxidants, such as ascorbyl palmitate, butylated hydroxyanisole (BHA), butylated hydroxytoluene (BHT), lecithin, propyl gallate, alpha-tocopherol, and the like; and metal chelating agents, such as citric acid, ethylenediamine tetraacetic acid (EDTA), sorbitol, tartaric acid, phosphoric acid, and the like.

Formulations of the present invention include those suitable for oral, nasal, topical, buccal, sublingual, rectal, vaginal and/or parenteral administration. The formulations may conveniently be presented in unit dosage form and may be prepared by any methods well known in the art of pharmacy. The amount of active ingredient that can be combined with a carrier material to produce a single dosage form will generally be that amount of the compound that produces a therapeutic effect. Generally, out of one hundred percent, this amount will range from about 1 percent to about ninety-nine percent of active ingredient, preferably from about 5 percent to about 70 percent, most preferably from about 10 percent to about 30 percent.

Methods of preparing these formulations or compositions include the step of bringing into association a compound of the present invention with the carrier and, optionally, one or more accessory ingredients. In general, the formulations are prepared by uniformly and intimately bringing into association a compound of the present invention with liquid carriers, or finely divided solid carriers, or both, and then, if necessary, shaping the product.

Formulations of the invention suitable for oral administration may be in the form of capsules, cachets, pills, tablets, lozenges (using a flavored basis, usually sucrose and acacia or tragacanth), powders, granules, or as a solution or a suspension in an aqueous or non-aqueous liquid, or as an oil-in-water or water-in-oil liquid emulsion, or as an elixir or syrup, or as pastilles (using an inert base, such as gelatin and glycerin, or sucrose and acacia) and/or as mouth washes and the like, each containing a predetermined amount of a compound of the present invention as an active ingredient. A compound of the present invention may also be administered as a bolus, electuary or paste.

Regardless of the route of administration selected, the compounds of the present invention and/or the pharmaceutical compositions of the present invention, are formulated into pharmaceutically acceptable dosage forms by conventional methods known to those of skill in the art.

Example 1

Effect of 4-(nitrooxy)butyl-(2S)-2-(6-methoxy-2-naphthyl) propanoate (naproxcinod) on Nitric Oxide Blood and cGMP Levels in Sickle Cell Mouse Model This trial was conducted to assess the efficacy of 4-(nitrooxy)butyl-(2S)-2-(6-methoxy-2-naphthyl) propanoate (naproxcinod) to increase Nitrite (a precursor to NO), and cGMP in Homozygous Townes Sickle Cell transgenic mice.

Experimental Design

Homozygous Sickle Cell transgenic mice were treated with either 4-(nitrooxy)butyl-(2S)-2-(6-methoxy-2-naphthyl) propanoate (naproxcinod) (15 mg/kg) or naproxen (15 mg/kg—as a control) or saline (as a vehicle control) by intravenous injection. After one hour, the mice were injected with thrombin (1 u/20 g) to induce platelet activation. Blood was drawn at 15, 30 and 1 hour after thrombin administration. Plasma nitrite levels were measured as a marker of nitric oxide bioavailability. cGMP levels were measured after addition of IBMX (3-Isobutyl-1-methylxanthine) (100 uM) to prevent cGMP degradation. Platelets were isolated and activation measured by surface expression of p-selectin.

Results

Figure 2:
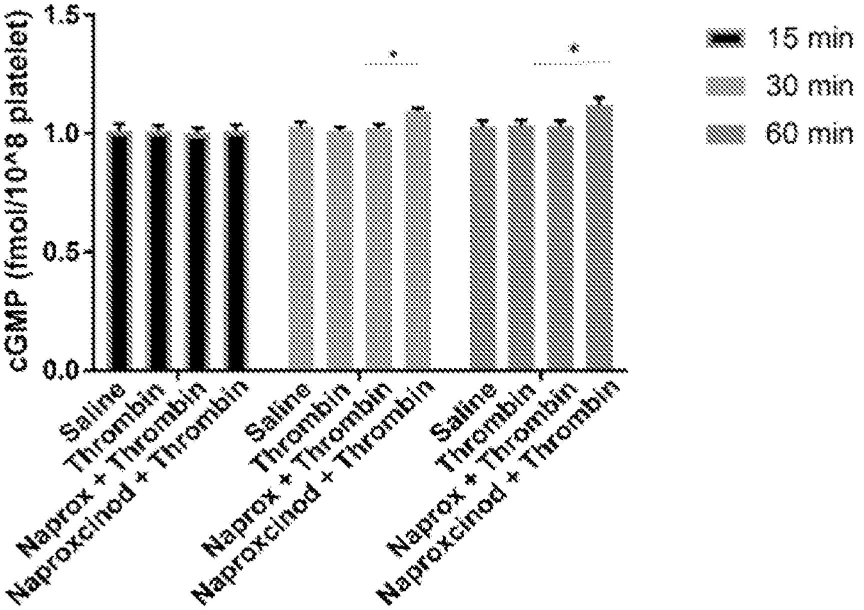
FIG. 2: is a graph showing cGMP concentrations (concentration-time) after intravenous administration of 4-(nitrooxy)butyl-(2S)-2-(6-methoxy-2-naphthyl) propanoate (naproxcinod) or naproxen in homozygous Sickle Cell transgenic mice.

At one-hour nitrite concentration was statistically greater with naproxcinod compared to thrombin alone or naproxen administration (FIG. 1). At 30 minutes and 60 minutes, cGMP levels were significantly increased ($p<0.01$) by naproxcinod compared to thrombin alone or naproxen administration (FIG. 2).

The data support the assertion that 4-(nitrooxy)butyl-(2S)-2-(6-methoxy-2-naphthyl) propanoate (naproxcinod) can be useful and helpful, in treating the recurrent ischemic crises in patients suffering from Sickle cell anemia, indeed 4-(nitrooxy)butyl-(2S)-2-(6-methoxy-2-naphthyl)propanoate is able to increase the cGMP level that mitigates the depletion of nitric oxide in Sickle cell disease and subsequently the vasculopathy, which are factors that contribute to the vaso-occlusive, in addition the anti-inflammatory component of the compound reduces inflammation and pain.

Thus while there have been described what are presently believed to be preferred embodiments of the invention, those skilled in the art will realize that changes and modifications may be made thereto without departing from the spirit of the invention, and it is intended to claim all such changes and modifications as fall within the true scope of the invention.

The invention claimed is:

1. A method for treating a vaso-occlusive crisis comprising administering a therapeutically effective amount of 4-(nitrooxy)butyl-(2S)-2-(6-methoxy-2-naphthyl) propanoate to a Sickle cell anemia patient, wherein the 4-(nitrooxy) butyl-(2S)-2-(6-methoxy-2-naphthyl) propanoate is administered in a dosage from 100 mg/day to 3000 mg/day.

2. The method according to claim 1 wherein the 4-(nitrooxy)butyl-(2S)-2-(6-methoxy-2-naphthyl) propanoate is administered during the prodromal phase of the vaso-occlusive crisis.

3. The method according to claim 1 wherein the method comprises reducing the severity or duration of the vaso-occlusive crisis.

4. The method according to claim 1 wherein the method comprises treating pain associated with the vaso-occlusive crisis.

5. The method according to claim 1 wherein the method comprises reducing or preventing organ and tissue damages caused by the vaso-occlusive crisis.

6. The method according to claim 1 wherein the therapeutically effective amount of 4-(nitrooxy)butyl-(2S)-2-(6-methoxy-2-naphthyl) propanoate is present in a pharmaceutical composition which further comprises one or more pharmaceutically acceptable carriers.

7. The method according to claim 6 wherein the pharmaceutical composition is suitable for oral, nasal, topical, buccal, sublingual, rectal, vaginal or parenteral administration.

8. A method for treating a vaso-occlusive crisis comprising administering a therapeutically effective amount of 4-(nitrooxy)butyl-(2S)-2-(6-methoxy-2-naphthyl) propanoate to a Sickle cell anemia patient, wherein the 4-(nitrooxy) butyl-(2S)-2-(6-methoxy-2-naphthyl) propanoate is administered in a dosage of from 15 to 22.5 mg per kg per day.

* * * * *